United States Patent [19]

Edwards et al.

[11] 4,198,404

[45] Apr. 15, 1980

[54] 6 ALPHA, 6 BETA-DIFLUORO-ETIANIC ACID DERIVATIVES

[75] Inventors: John A. Edwards, Los Altos; Francisco S. Alvarez, Sunnyvale, both of Calif.

[73] Assignee: Syntex (U.S.A.) Inc., Palo Alto, Calif.

[21] Appl. No.: 893,386

[22] Filed: Apr. 5, 1978

[51] Int. Cl.$^2$ ............................................. A61K 31/56
[52] U.S. Cl. ................................. 424/243; 260/397.1
[58] Field of Search ....................... 260/397.1; 424/243

[56] References Cited

U.S. PATENT DOCUMENTS

| | | | |
|---|---|---|---|
| 3,546,215 | 12/1970 | Fried | 260/239.55 |
| 4,093,721 | 6/1978 | Phillipps et al. | 424/243 |

Primary Examiner—Elbert L. Roberts
Attorney, Agent, or Firm—Tom M. Moran; Gerard A. Blaufarb

[57] ABSTRACT

Certain 3-ketoandrost-4-ene and 3-ketoandrosta-1,4-diene 17 beta-carboxylic acids and esters substituted at the 6 alpha and 6 beta positions with fluorine substituents are useful as anti-inflammatory steroids. These compounds are optionally substituted at the 9 alpha position with fluoro, chloro or bromo; substituted at the 11 with a keto, a beta-hydroxy or a beta-chloro (the latter only when there is a 9 alpha-chloro); substituted at 16 alpha (or 16 beta) with methyl or hydrogen when there is a 17 alpha-hydroxy (or an ester).

8 Claims, No Drawings

6 ALPHA, 6 BETA-DIFLUORO-ETIANIC ACID DERIVATIVES

BACKGROUND OF THE INVENTION

1. Field of the Invention

This invention relates to novel 3-keto-androst-4-ene-17 beta-carboxylic acids, the corresponding androsta-1,4-dienes, the 17 alpha-alkanoyloxy derivatives and the alkyl, phenyl and benzyl 17 beta-carboxylates thereof. More specifically it relates to these compounds which are substituted at the 6 alpha, and 6 beta positions with fluorine. The 17 beta-carboxylates, especially the 17 beta-methyl carboxylates are active anti-inflammatory agents in mammals. The invention further relates to pharmaceutically active compositions comprising an active compound of the invention in combination with a pharmaceutically acceptable excipient.

2. Prior Art

3-Keto-androst-4-ene 17 beta-carboxylic acids which are substituted at the 9 position with chlorine or fluorine and at the 11 position with keto or hydroxy or chloro group are known. See for example U.S. Pat. No. 3,828,080. It is also known that 3-keto-androst-4-ene 17 beta-carboxylic acids may be substituted at both the 9 alpha and 6 alpha positions with fluorine. See for example U.S. Pat. No. 3,636,010. A heretofore unknown series of -3-keto-androst-4-ene 17 beta-carboxylic acids being substituted at the 6 alpha and 6 beta positions with fluorine has been discovered and is disclosed herein. The compounds exhibit good anti-inflammatory activity while exhibiting little adverse systemic activity.

SUMMARY OF THE INVENTION

One aspect of this invention is a compound chosen from those represented by the formula (I)

[Structure (I)]

wherein
$X^1$ is hydrogen, fluoro, chloro or bromo;
$X^2$ is $$=C=O \text{ or } =C\begin{matrix}OH\\H\end{matrix} \text{ or is } =C\begin{matrix}Cl\\H\end{matrix}$$

when $X^1$ is chloro;
R is hydrogen, alkyl of 1 through 6 carbon atoms, optionally substituted with one halo substituent, or phenyl or benzyl optionally substituted with a substituent which is alkyl of 1 through 4 carbon atoms, alkoxy of 1 through 4 carbon atoms or halo;
$R^1$ is hydrogen or alkanoyl of 2 through 6 carbon atoms;
$R^2$ is hydrogen, alpha-methyl or beta-methyl; and
the bond between C-1 and C-2 is a double or single bond.

Another aspect of this invention is an anti-inflammatory pharmaceutical composition which comprises a suitable pharmaceutical excipient in combination with an effective amount of a compound chosen from those represented by Formula (I), above, wherein each of the substituents are as defined except that R is not hydrogen. Particularly valuable compounds in this composition are set forth hereinafter.

Still another aspect of this invention is a process for treating an inflamed condition in mammals which comprises treating the afflicted mammal with an effective amount of a compound chosen from those represented by formula (I), above, wherein substituents are as defined above except that R is not hydrogen.

DETAILED DESCRIPTION AND PREFERRED EMBODIMENTS

Compounds

In its broadest aspect, this invention is a compound chosen from those represented by formula (I), above, wherein
$X^1$ is hydrogen, fluoro, chloro or bromo;
$X^2$ is $$=C=O \text{ or } =C\begin{matrix}OH\\H\end{matrix} \text{ or is } =C\begin{matrix}Cl\\H\end{matrix}$$

when $X^2$ is chloro;
R is hydrogen, alkyl of 1 through 6 carbon atoms optionally substituted with one halo substituent, or phenyl or benzyl optionally substituted with alkyl of 1 through 4 carbon atoms, alkoxy of 1 through 4 carbon atoms or halo;
$R^1$ is hydrogen or alkanoyl of 2 through 6 carbon atoms;
$R^2$ is hydrogen, alpha-methyl or beta-methyl; and
the bond between C-1 and C-2 is a double or single bond.

One subgroup of the broad aspect of the invention comprises those compounds represented by the formula (I) wherein $X^1$, $X^2$ and R and $R^1$ are as defined previously and $R^2$ is alpha-methyl.

Another subgroup comprises those compounds of formula (I) wherein $X^1$ and $X^2$ are as defined previously; R is alkyl of 1-6 carbon atoms, phenyl or benzyl; $R^1$ is hydrogen or alkanoyl of 2 through 6 carbon atoms; and $R^2$ is alpha-methyl.

Another subgroup of the broad aspect of this invention comprises those compounds represented by formula (I)
wherein
$X^1$ is as defined previously; $X^2$ is $$=C\begin{matrix}OH\\H\end{matrix} \text{ or is } =C\begin{matrix}Cl\\H\end{matrix}$$

when $X^1$ is chloro;
R is alkyl of 1–6 carbon atoms, phenyl or benzyl;
R' is alkanoyl of 2–6 carbon atoms;
and $R^2$ is alpha-methyl.

Of this subgroup those compounds wherein $X^1$ is fluoro and $X^2$ is

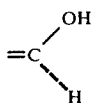

and those wherein $X^1$ is chloro and $X^2$ is

are preferred.

In defining the compounds of this invention alkyl of 1 through 6 carbon atoms includes both straight chain and branched alkyl groups such as methyl, ethyl, n-propyl, isopropyl, n-butyl, isobutyl, t-butyl, pentyl, iso-amyl, n-hexyl and the like. These alkyls are optionally substituted with a halogen atom such as fluorine, chlorine, bromine or iodine e.g. fluoromethyl, 2-chloro-ethyl, 3-bromopropyl, 4-bromo-n-butyl, and the like. The phenyl and benzyl substituents may be substituted on the phenyl ring at the 2, 3 or 4-positions with one substituent such as alkoxy (e.g. methoxy, ethoxy, n-propoxy, t-butoxy and the like), alkyl of 1-4 carbons (e.g. methyl, ethyl, isopropyl, n-propyl, t-butyl, n-butyl, etc.), or a halo such as fluoro, chloro, bromo or iodo. Preferably the substitution is at the 2 or 4 positions.

In naming the compounds of this invention the substituents present on the androstane ring shall be included alphabetically and the compounds shall be alkyl (or phenyl or benzyl) 17 beta-carboxylates. For example, if in formula (I), above, $X^1$ is chloro, $X^2$ is

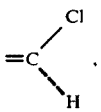

R is methyl, $R^1$ is acetoxy and $R^2$ is alpha-methyl the name is methyl 17 alpha-acetoxy-9 alpha,11 beta-dichloro-6 alpha,6 beta-difluoro-16 alpha-methyl-3-oxoandrosta-1,4-diene-17 beta-carboxylate. If on the other hand, R is hydrogen but $X^1$, $X^2$, $X^3$, $X^4$, $R^1$ and $R^2$ are the same the compound is named 17 alpha-acetoxy-9 alpha,11 beta-dichloro-6 alpha,6 beta-difluoro-16 alpha-methyl-3-oxoandrosta-1,4-diene 17 beta-carboxylic acid.

Process For Preparing The Compounds Of The Invention

The process for preparing the compounds of the invention is essentially a two-part process which may be carried out in any order. One part is to eliminate the 21 carbon atom from a suitable 21-hydroxy (or a suitable ester thereof) 6 alpha-fluoro pregnane and the other part is to fluorinate, at the 6 beta-position. A process may be represented by Reaction Sequence (A) wherein R is a suitable alkyl of 1-6 carbon atoms, benzyl or phenyl; R' is alkanoyl of 2-6 carbon atoms; $R^2$ is alpha-methyl, beta-methyl or hydrogen; $R^3$ is alkanoyl of 2-6 carbons; and $R^4$ is methyl or ethyl.

From Reaction Square A, it is seen that the fluorination is a two step process, the elimination of the 21-carbon atom is essentially a one step process, and the other steps are performed to protect hydroxy or acid groups from reaction.

The elimination of a 21 carbon atom from a suitable pregnane represented by formula (I) is readily accomplished by any means known in the art such as using sodium hypobromite or hypoiodite as taught in U.S. Pat. No. 2,769,822 or by using sodium periodate. Preferably, however, the elimination of the 21 carbon atom is carried out by using an alkali metal carbonate in alcohol in the presence of oxygen as described in PA-880, filed even date herewith. In the latter case the reaction is carried out at room temperature and atmospheric pressure while the source of oxygen is preferably air. Generally the reaction will be completed within less than 72 hours with a constant stream of air being bubbled into a stirred reaction mixture to give a compound of formula (2).

Once a compound represented by Formula (2) is obtained it is first reacted with an appropriate alkanoyl anhydride, such as propionic anhydride, acetic anhydride, butyric anhydride, caproic anhydride and the like in the presence of a suitable organic base such as pyridine in an inert solvent. Preferably the solvent is the anhydride itself which is present at a substantial molar excess over the reactant represented by Formula (2). This results in a compound represented by Formula (3) wherein $R^1$ is alkanoyl of 2-6 carbon atoms. The compound is readily precipitated from the organic solvent by adding water, and the precipitate is then readily filtered and dried in preparation for the next step.

In the next step the compound represented by Formula (3) is reacted with a suitable alkyl or benzyl iodide in the presence of a suitable inert solvent such as dimethyl foramide or dimethyl acetamide along with a weak base such as sodium bicarbonate. A phenyl ester can be obtained by the reaction of the free acid (3) with a phenol in an inert solvent in the presence of dicyclohexylcarbodiimide according to the principles set forth in Neelakantan et al, *New Reagents for the Synthesis of Depsides,* Tetrahedron 21, 3531-3536 (1965). The resulting compound represented by Formula (4) is readily precipitated from the reaction mixture by adding water, the precipitate is filtered and air dried to afford a compound which is then reacted with an alkanoyl anhydride such as acetic anhydride in a suitable amine such as trimethyl amine in the presence of a catalytic amount of dimethylaminopyridine to form a compound represented by Formula (5) wherein $R^3$ is alkanoyl of 2-6 carbon atoms. The reaction generally takes place at room temperature. By cooling the resulting reaction mixture to about 0° C. and fully diluting with water a precipitate forms which is readily collected by filtration and air dried to give a product represented by (5) which is then used for the next step.

The 3-enol ether of formula (6) where $R^4$ is methyl or ethyl is prepared by treating the compounds of formula (5), by with an alkyl orthoformate, preferably methyl orthoformate or ethylorthoformate, in the presence of an acid catalyst, such as sulfuric acid, p-toluenesulfonic acid, and the like, in an inert non-aqueous, preferably anhydrous, organic solvent, e.g. methanol or ethanol, to afford the compounds of formula (6) which is then isolated by conventional techniques; for example, the reaction mixture is neutralized and water is added to crystallize the enol ether derivative. The solid is then collected by filtration. The resulting compound is then treated with perchloryl fluoride in a mixture of 90% acetone 10% water at room temperature to furnish a compound of formula (7). The reaction is conducted at temperatures in the range of from about −78° C. to about room temperature (RT), preferably starting at −78° C. and slowly allowing the mixture to warm to RT. About 0.9–1.1 molar equivalents of perchloryl fluoride for each mole of the compound of formula (6) are utilized.

The novel 6 alpha,6 beta-difluoro steroids, the compounds of formula (7), are isolated by conventional techniques. For example, the reaction mixture is cautiously neutralized with an aqueous basic solution and the novel product is precipitated by the addition of water and elimination of the acetone followed by chromatography on silica gel. The solid product is collected by filtration. The product can then be purified by dissolving in an inert organic solvent, immiscible with water, as for example, a halogenated hydrocarbon, such as methylene chloride, or a water-immiscible ether, such as diethylether; washing with water to neutrality, drying and evaporating to dryness. The product can be further purified by recrystallization, chromatography, and the like.

The unsaturation at the C 1-2 double bond, is introduced into the novel compounds of formula (7) by conventional techniques to furnish the novel compounds of formula (8). For example, the novel compounds of formula (7) can be refluxed with selenium dioxide in the presence of t-butanol and pyridine, or refluxed with selenium dioxide and chlorobenzene, or refluxed with 2,3-dichloro-5,6-dicyano-1,4-benzoquinone in dioxane in the presence of catalytic amounts of p-toluene sulfuric acid to afford the compounds of formula (8).

The compound represented by Formula (8) is thereafter hydrolyzed in mixing it with a suitable solvent such as methanol and stirring with a one molar solution of a strong base such as sodium or potassium hydroxide (anhydrous) until the acetyl portion $R^3$ is hydrolyzed to form a compound represented by Formula 9. The reaction mixture is acidified with a suitable organic acid such as glacial acetic acid and concentrated under reduced pressure to a small volume. Water is added while methanol is continually removed under reduced pressure. The residue is extracted from the aqueous mixture with dichloromethane to give a solution which is then dried with sodium sulfate, filtered and the dichloro methane is removed under pressure to give a product represented by (9).

The compound so prepared is then reacted at low temperatures of about 0°–10° C. with thionyl chloride and anhydrous pyrridine. The thionyl chloride is added slowly to the pyrridine/compound (9) mixture to give a compound represented by Formula (10) which has a double bond between carbons 9 and 11. Alternatively the 11-hydroxy steroid of compound (9) may be treated with mesyl chloride and dimethyl formamide or dichloromethane in the presence of pyridine containing a catalytic amount of sulfur trioxide (about 5% as compared to the mesyl chloride). The desired steroid having double bond at 9,11 is precipitated from the reaction mixture by slowly adding water at low temperatures such as 0° to 10° C. until a precipitate is formed which is then collected by filtration, water washed and dried.

The 9 alpha,11 beta-fluorhydrin (13); 9 alpha,11 beta-chlorhydrin (15); 9 alpha,11 beta-bromhydrin (11); and 9 alpha,11 beta-dichloro compounds (14) are readily prepared from the compound of formula (10) by methods known in the art. The 9 alpha,11 beta-bromhydrin is prepared by treating the compound of formula (10) with N-bromo acetamide and perchloric acid in dioxane or tetrahydrofuran. The resulting 9-bromo-11-hydroxy steroid (11) is treated at room temperature (20°–25° C.) with sodium hydroxide in methanol to give a 9 beta,11 beta oxido steroid represented by formula (12). This in turn is treated with hydrogen chloride or hydrogen fluoride in an inert, nonaqueous, preferably anhydrous, solvent or mixture of such solvents. For example, see U.S. Pat. No. 3,211,758 to Tarkoey wherein a hydrogen fluoride/urea complex is employed.

The 9 alpha,11 beta-dichloro compound (14) is prepared by treating the corresponding 9(11)-pregnene with chlorine gas in chloroform in the presence of pyridine at about 0°—about 30° C.

Alternatively the compounds of the invention may be prepared according to the reaction sequence B starting from known 6 alpha,6 beta-difluoro 21 hydroxy pregna-1,4-dienes. The compounds represented by formula (16) are known in the art as taught in U.S. Pat. No. 3,546,215 Fried. The 21 carbon is eliminated from the compound represented by formula (16) by methods discussed hereinbefore. The resulting compound represented by formula (17) is either esterified to form a compound represented by formula (18) as discussed hereinbefore or a compound represented by formula 19 as discussed hereinbefore.

In Reaction Sequence (C) the 21-carbon atom is not removed until the second to the last step; however, the reaction conditions for preparing the intermediates are similar to analogous reactions discussed for Reaction Sequences A dn B hereinbefore.

In the first step of Reaction Sequence (C) a compound of formula (21) is converted into a compound of formula (22) by reacting the former with a suitable anhydride such as acitic anhydride with ethyl amine and dimethylaminopyridine under conditions discussed in regard to converting a compound of formula (4) to (5) in Reaction Sequence (A). The next two steps, i.e. fluorination of compound (22) to form compound (24) are essentially the same as discussed for fluorinating compound (5) to form a compound of formula (7) in Reaction Sequence (A). The hydrolysis of the compound of formula (24) takes place using a suitable base such as anhydrous sodium carbonate in methanol at room temperature to form compound (25) which in turn is treated by methods discussed above to remove the 21-carbon and form the 17 beta-carboxylic acid (26). The corresponding 17 alpha-alkanoate (27) is formed by reacting with an appropriate anhydride.

A 16 methyl group is introduced by treating the corresponding 20-keto-pregn-16-ene with methyl magnesium bromide in the presence of cuprous chloride in an ether such as tetrahydrofuran. The 20-keto-pregn-16-ene is prepared by preparing the 3,20-bis-semicarbazone of a 3,20-diketo 17 alpha-hydroxy steroid, treating it with glacial acetic acid and acetic anhydride and then allowing the resulting product to react with aqueous pyruvic acid.

The 17 alpha-hydroxy group is introduced in conjunction with 16 beta-methyl group by first treating the corresponding 16-methyl-pregn-16-ene (which is prepared by treating the corresponding pregn-16-ene with diazomethane and then heating the resulting product to 180° C.) with hydrogen peroxide in an aqueous basic media, then permitting the resulting 16,17-oxido-16-methyl steroid to react with hydrogen bromide in glacial acetic acid. The resulting 16,17-bromohydrin is hydrogenated with the use of a palladium catalyst to afford the corresponding 16 beta methyl-17 alpha-hydroxy derivative.

The 17 alpha-hydroxy group is introduced in conjunction with the 16 alpha-methyl by methods known in the art, such as the method described by Edwards et al in the Journal of the American Chemical Society 82, 2318–22, 1960. In this process an appropriate 21-substituted 16 alpha-methylpregna-1,4-diene-3,2-dione is converted to 20-enol acetate by refluxing with acetic anhydride and freshly distilled acetyl chloride. The 20-enol acetate is recovered and reacted with monoperphthalic acid in ether and benzene to form the 17,20-epoxide which in turn is treated with methanol and aqueous potassium hydroxide to give the 16 alpha-methyl-17 alpha-hydroxy steroid which is isolated by means known in the art.

Administration and Formulation

The compounds of this invention are useful for the relief of inflamed conditions in mammals, and more specifically are useful for relieving inflammatory manifestations of corticosteroid responsive dermatoses. Initial approximation of anti-inflammatory activity is done by the following procedure of McKenzie, S. W. and Stoughton, R. B., "Method for Comparing Percutaneous Absorption of Steroids" Arch Dermat, 86, 608 (1962) or modifications thereof.

Generally, the inflammatory manifestation in mammals, particularly humans, is combatted by treating the afflicted mammal with a therapeutically effective amount of the novel steroids of this invention, that is an amount which results in improvement of the inflamed condition. Preferably the steroids are first formulated to prepare a suitable pharmaceutical formulation, as discussed hereinafter, which is then placed in contact with the afflicted area. An effective amount will depend upon the particular condition and the animal receiving the treatment but will vary between 0.001% to 10% by weight of the pharmaceutical composition and preferably will be between 0.02 and 1% by weight of the formulation. Using these levels in the formulation, a therapeutically effective and non-side effect producing amount, i.e. enough to effect an anti-inflammatory response, but not enough to adversely effect the recipient, is applied to the inflamed area.

The compounds of this invention not only have anti-inflammatory activity but also exhibit a low level of systemic activity, as measured by recognized laboratory assays. This allows for the application of an effective amount of the anti-inflammatory compounds with little adverse effect on the rest of the animal's system.

The novel steroids of this invention may be formulated with suitable pharmaceutical excipients known in the art to form particularly effective, anti-inflammatory compositions which are administered orally, nasally, rectally, or, preferably, topically. Generally an effective amount of the steroid is about 0.001%w to about 10%w of the total formulated composition. The rest of the formulated composition will be about 90%w to about 99.999%w of a suitable excipient which may include a pharmaceutically acceptable solvent and other pharmaceutically acceptable additives to form an effective pharmaceutical formulation.

A pharmaceutically acceptable solvent is one which is substantially non-toxic and non-irritating under the conditions used and may be readily formulated into any of the classical drug formulations such as powders, creams, ointments, lotions, gels, foams, suppositories, aerosols, solutions or the like. Particularly suitable solvents include water, glycerine, propylene carbonate, and a glycol such as 1,2-propylene diol (i.e. propylene glycol), 1,3-propylene diol, polyethylene glycol having a molecular weight of from 100 to 10,000, dipropylene glycol, etc.; and mixtures of the aforementioned with each other.

A topical cream may be prepared as a semi-solid emulsion of oil in water or water in oil. A cream base formulation by definition is an emulsion which is a two-phase system with one liquid (for example fats or oils) being dispersed as small globules in another substance (e.g., a glycol-water solvent phase) which may be employed as the primary solvent for the novel steroids therein, the cream formulation may contain fatty alcohols, surfactants, mineral oil or petrolatum and other typical pharmaceutical adjuvants such as anti-oxidants, antiseptics, or compatible adjuvants. A typical cream base formulation is given in the following table:

| | |
|---|---|
| Water/glycol mixture (15% or more glycol) | 50–99 parts by weight |
| Fatty alcohol | 1–20 |
| Non-ionic Surfactant | 0–10 |
| Mineral oil | 0–10 |
| Typical pharmaceutical adjuvants | 0–5 |
| Active Ingredients | 0.001–10 |

The fatty alcohol, non-ionic surfactant, and other adjuvants are discussed in U.S. Pat. No. 3,934,013 to Poulsen which is incorporated herein by reference.

The novel steroids of this invention may also be formulated as ointments. A "classical" ointment is semi-solid anhydrous composition which may contain mineral oil, white petrolatum, a suitable solvent such as a glycol and may include propylene carbonate and other pharmaceutically suitable additives such as surfactants, for example Span and Tween, or wool fat (lanolin), along with stabizers such as antioxidants and other adjuvants as mentioned before. Following is an example of a typical "classical" ointment base:

| | |
|---|---|
| White petrolatum | 40–94 parts by weight |
| Mineral Oil | 5–20 |
| Glycol solvent | 1–15 |
| Surfactant | 0–10 |
| Stabilizer | 0–10 |
| Active Ingredients | 0.001–10.0 |

Other suitable ointment base formulations which employ propylene carbonate are described in U.S. Pat. No. 4,017,615 issued Apr. 12, 1977 by Shastri et al entitled "Propylene Carbonate Ointment Vehicle" and U.S. Pat. No. 3,924,004 issued Dec. 2, 1975 by Chang et al entitled "Fatty Alcohol-Propylene Carbonate-Glycol Solvent Cream Vehicle". As much of those applications as is pertinent is incorporated herein by reference. Following is a typical ointment base formulation containing propylene carbonate:

| | |
|---|---|
| Active Ingredients | 0.001–10.0 parts by weight |
| Propylene Carbonate | 1–10 |
| Solvent | 1–10 |
| Surfactant | 1–10 |
| White Petrolatum | 70–97 |

Suitable solvents, surfactants, stabilizers, etc. are discussed in U.S. Pat. No. 3,934,013 and such discussion is incorporated hereinby reference.

A suitable "non-classical" anhydrous, water washable "ointment type" base is described in U.S. Pat. No. 3,952,930 to Katz and Neiman, and that patent is incorporated herein by reference. A representative composition of this invention utilizing such a base is as follows:

| Glycol solvent | 50-35 parts by weight |
|---|---|
| Fatty alcohol | 15-45 |
| Compatible plasticizer | 0-15 |
| Compatible coupling Agent | 0-15 |
| Penetrant | 0-20 |
| Active Ingredients | 0.001-10.0 |

Specific embodiments of the process of this invention are found in the following Examples which are given by way of illustration only and not to be interpreted as limiting the scope of the claims appended hereto.

EXAMPLE 1

This example sets forth a process for preparing benzyl or alkyl 11 beta-acetoxy-6 alpha,6 beta-difluoro-17 alphaalkanoyl-16 alpha-methyl-3-oxo-androst-4-ene 17 beta-carboxylates.

A. Preparation of methyl 11 beta-acetoxy-6 alpha,6 beta-difluoro-16 alpha-methyl-3-oxo-17 alpha-propionyloxyandrost-4-ene 17 alpha-carboxylate.

A solution of 86 grams (g) of 21-acetoxy-6 alpha-fluoro-11 beta,17 alpha-dihydroxy-16 alpha-methyl-pregn-4-ene-3,20-dione in 1000 milliliters (ml) of methanol plus 86 g of anhydrous potassium carbonate is stirred magnetically for about 20 hours while air is bubbled through the solution. The methanol is then eliminated to leave yellowish precipitate in the reaction vessel to which is added 1.5 liters (l) of water. The resulting mixture is stirred while an air current is continued for another 72 hours. Additional methanol is added at intervals to maintain a volume of about 1.5 liters. Analysis by thin layer chromatography (TLC) using 5% methanol/1% acetic acid/94% dichloromethane (DCM) shows only the presence of 6 alpha-fluoro-11 beta,17 alpha-dihydroxy-16 alpha-methyl-3-oxoandrost-4-ene-17 beta-carboxylic acid. The reaction mixture is acidified with concentrated hydrochloric acid to pH 2, and the crystalline precipitate was collected by filtration and air dried to yield 36.41 g of 6 alpha-fluoro-11 beta,17 alpha-dihydroxy-16 alpha-methyl-3-oxoandrost-4-ene-17 beta-carboxylic acid, melting point (mp) 257°-260° C.; $\lambda_{max}^{methanol}$ 320, 237 nm ($\epsilon$ 125, 13589).

A mixture of 10 g of 6 alpha-fluoro-11 beta,17 alpha-dihydroxy-16 alpha-methyl-3-oxoandrost-4-ene 17 beta-carboxylic acid in 5 ml of triethyl amine and 5 ml of propionic anhydride is stirred at room temperature for a period of 12 hours. The reaction mixture is cooled in an icewater bath and slowly diluted with water up to 500 ml. The crystalline precipitate so obtained is collected by filtration, washed with water and air dried to give 6 alpha-fluoro-11 beta-hydroxy-16 alpha-methyl-3-oxo-17 alpha-propionyloxyandrost-4-ene 17 beta-carboxylic acid in about 90% theoretical yield.

A suspension of 10 g of 6 alpha-fluoro-11 beta-hydroxy-16 alpha-methyl-3-oxo-17 alpha-propionyloxyandrost-4-ene 17 beta-carboxylic acid prepared in this manner in 100 ml of dimethyl formamide is mixed with 10 g of methyl iodide and stirred in the presence of 10 g of sodium bicarbonate for 12 hours. The reaction mixture is slowly diluted with water to give a crystalline precipitate of methyl 6 alpha-fluoro-11 beta-hydroxy-16 alpha-methyl-3-oxo-17 alpha-propionyloxyandrost-4-ene 17 beta-carboxylate, which is collected by filtration and air dried. Ten g of the resulting product is dissolved in 5 ml of acetic anhydride and 5 ml of triethylamine. The resulting solution is treated at room temperature with 1 g of dimethylamino pyridine for a period of 4 hours. The reaction mixture is cooled in an ice-water bath, and slowly diluted with water up to 500 ml. The crystalline precipitate so obtained is collected by filtration and air dried to give methyl 11 beta-acetoxy-6 alpha-fluoro-16 alpha-methyl-3-oxo-17 alpha-propionyloxyandrost-4-ene 17 beta-carboxylate.

Ten g of methyl 11 beta-acetoxy-6 alpha-fluoro-16 alpha-methyl-3-oxo-17 alpha-propionyloxyandrost-4-ene 17 beta carboxylate prepared in this manner are dissolved in 100 ml of DCM and treated with 5 ml of triethylorthoformate at room temperature in the presence of 1 g of paratoluenesulfonic acid monohydrate for a period of 3 hours. The reaction mixture is basified by the addition of 5 ml of triethyl amine, and the reaction mixture is concentrated to dryness under reduced pressure to leave a residue of methyl 11 beta-acetoxy-3-ethoxy-6 alpha-fluoro-16 alpha-methyl-17 alpha-propionyloxyandrosta-3,5-diene 17 beta-carboxylate.

Ten g of methyl 11 beta-acetoxy-3-ethoxy-6 alpha-fluoro-16 alpha-methyl-17 alpha-propionyloxyandrost-4-ene 17 beta-carboxylate prepared in this manner are dissolved in 250 ml of a mixture of 90% acetone/10% water. Perchloryl fluoride is slowly bubbled through the solution at room temperature until TLC analysis using 35% ethyl acetate/65% hexane indicates the reaction is complete. When the reaction is complete, the mixture is diluted with 250 ml of water, and the acetone is eliminated under reduced pressure. The resulting mixture is extracted three times with DCM, dried over anhydrous sodium sulfate, filtered and concentrated to dryness under reduced pressure. The residue is dissolved in a mixture of 75% DCM/25% hexane, and chromatographed over a column of 250 g of silica gel eluting with the same solvent. The homogeneous fractions are combined, concentrated to dryness, and the residue is further purified by crystallization to afford methyl 11 beta-acetoxy 6 alpha,6 beta-difluoro-16 alpha-methyl-3-oxo-17 alpha-propionyloxyandrost-4-ene 17 beta-carboxylate.

B. Similarly, by following the procedure set forth in this example, but substituting other suitable anhydrides such as acetic anhydride, butyric anhydride, valeric anhydride, caproic anhydride, etc. for propionic anhydride, and/or other suitable alkyl or benzyl iodides such as ethyl iodide, n-propyl iodide, i-butyl iodide, n-hexyl iodide, benzyl iodide, 4-chlorobenzyl iodide, 4-ethoxybenzyl iodide for methyl iodide, other alkyl or benzyl 11 beta-acetoxy 17 alpha-alkanoyloxy-6 alpha,6 beta-difluoro 16 alpha-methyl-3-oxoandrost-4-ene 17 beta-carboxylates are prepared.

EXAMPLE 2

This example sets forth a process for converting an androst-4-ene into the corresponding androsta-1,4-diene.

A. Preparation of methyl 11 beta-acetoxy-6 alpha, 6 beta-difluoro-16 alpha-methyl-3-oxo-17 alpha-propionyloxyandrost-1,4-diene 17 beta-carboxylate.

A mixture of 5 g of methyl 11 beta-acetoxy-6 alpha,6 beta-difluoro-16 alpha-methyl-3-oxo-17 alpha-propionyloxyandrost-4-ene 17 beta-carboxylate prepared in accordance to the process of Example 1, Part A, in 50 ml of dioxane plus 4.5 g of dichlorobenzoquinone is refluxed for 24 hours in the presence of 250 mgs of paratoluenesulfonic acid. The mixture is cooled to room temperature, and diluted with 250 ml of DCM. The crystalline precipitate of dihydrodiaryanodichlorobenzoquinone is eliminated by filtration, washing with DCM. The filtrates plus washings are combined and concentrated to dryness under reduced pressure. The residue is dissolved in DCM and filtered through a column of neutral aluminum oxide, eluting with DCM. The honogeneous fractions are combined and concentrated to dryness under reduced pressure. The residue was purified further by crystallization to give methyl 11 beta-acetoxy-6 alpha,6 beta-difluoro-16 alpha-methyl-3-oxo-17 alpha-propionyloxyandrosta-1,4-diene 17 beta-carboxylate.

B. Similarly, by following the procedure of Part A of this example, but substituting the alkyl or benzyl 11 beta-acetoxy-17 alpha-alkanoyloxy-6 alpha,6 beta-difluoro-16 alpha-methyl-3-oxoandrost-4-ene 17d beta-carboxylates prepared according to the process of Part B, Example 1, the corresponding alkyl or benzyl 11 beta-acetoxy-17 alpha-alkanoyloxy-6 alpha,6 beta-difluoro-16 alpha-methyl-3-oxoandrosta-1,4-diene 17 beta-carboxylates are prepared.

EXAMPLE 3

This example sets forth a process for hydrolyzing an ester of 11 beta-acetoxyandrost-4-ene or an 11 beta-acetoxyandrosta-1,4-diene 17 beta-carboxylic acid to the corresponding 11 beta-hydroxy compound.

A. A solution of 5 g of methyl 11 beta-acetoxy-6 alpha,6 beta-difluoro-16 alpha-methyl-3-oxo-17 alpha-propionyloxyandrosta-1,4-diene 17 beta-carboxylate (made according to the process of Example 2, Part A) in 100 ml methanol is treated at room temperature with 250 ml of a 1 M solution of sodium hydroxide (anhydrous) for a period of five hours. The reaction mixture is acidified with glacial acetic acid, and then concentrated under reduced pressure to a small volume. Water is then added and the elimination of the methanol is continued under reduced pressure. The residue is extracted from the aqueous mixture with DCM. The DCM solution is dried over anhydrous sodium sulfate, filtered, and the DCM is removed under reduced pressure. The residue is crystallized from ethyl acetate/hexane to give methyl 6 alpha,6 beta-difluoro-11 beta-hydroxy-16 alpha-methyl-3-oxo-17 alpha-propionyloxyandrosta-1,4-diene 17 beta-carboxylate.

EXAMPLE 4

This example sets forth a process for preparing alkyl or benzyl 17 alpha-alkanoyloxy-9 alpha-bromo (or 9 alpha-chloro)-6 alpha,6 beta-difluoro-11 beta-hydroxy-16 alpha-methyl-3-oxoandrosta-1,4-diene 17 beta-carboxylates.

A. Preparation of methyl 9 alpha-bromo-6 alpha,6 beta-difluoro-11 beta-hydroxy-16 alpha-methyl-3-oxo-17 alpha-propionyloxyandrosta-1,4-diene 17 beta-carboxylate.

A solution of 10 g of methyl 6 alpha,6 beta-difluoro-11 beta-hydroxy-16 alpha-methyl-3-oxo-17 alpha-propionyloxyandrosta-1,4-diene 17 beta-carboxylate prepared in the manner set forth in Example 3, Part A, in 100 ml of anhydrous pyridine is cooled to 0°–5° C. by means of an external ice-water bath, and 10 ml of thionyl chloride is added dropwise to the resulting solution over a period of 10 minutes. The reaction mixture is then kept at 0°–5° C. for an additional 30 minutes. The mixture is slowly diluted up to 2 liters with water. The crystalline precipitate so obtained is collected by filtration, washed with water and air dried to give methyl 6 alpha,6 beta-difluoro-16 alpha-methyl-3-oxo-17 alpha-propionyloxyandrosta-1,4,9(11)-triene 17 beta-carboxylate.

A suspension of 10 g of methyl 6 alpha,6 beta-difluoro-16 alpha-methyl-3-oxo-17 alpha-propionyloxyandrosta-1,4,9(11)-triene 17 beta-carboxylate prepared in this manner in 10 ml of p-dioxane is treated with 9 g of dibromohydantoin in the presence of 1 ml of 70% perchloric acid and 10 ml of water at room temperature for a period of 5 hours. The reaction mixture is slowly diluted with water up to 2 liters. The resulting crystalline precipitate is collected by filtration, washed with water and air dried, to yield methyl 9 alpha-bromo-6 alpha,6 beta-difluoro-11 beta-hydroxy-16 alpha-methyl-3-oxo-17 alpha-propionyloxy-androsta-1,4-eiene 17d beta-carboxylate.

B. By following in principle the procedure set forth in Part A of this example but substituting 1,3-dichloro-5,5-dimethylhydantoin for dibromohydantoin, methyl 9 alpha-chloro-6 alpha,6 beta-difluoro-11 beta-hydroxy-16 alpha-methyl-3-oxo-17 alpha-propionyloxyandrosta 1,4 diene 17 beta-carboxylate is prepared.

C. Similarly, by following in principle the procedure set forth in Parts A and B of this example, but substituting other suitable alkyl or benzyl 17 alpha-alkanoyloxy-6 alpha,6 beta-difluoro-11 beta-hydroxy-16 alpha-methyl-3-oxoandrosta-1,4-diene 17 beta-carboxylates for methyl 6 alpha,6 beta-difluoro-11 beta-hydroxy-16 alpha-methyl-3-oxo 17 alpha-propionyloxy-androsta-1,4-diene 17 beta-carboxylate, other compounds are prepared such as ethyl 9 alpha-bromo-6 alpha,6 beta-difluoro-11 beta-hydroxy-16 alpha-methyl-3-oxo-17 alpha-propionyloxy-androsta-1,4-diene 17 beta-carboxylate;

ethyl 17 alpha-acetoxy-9 alpha-chloro-6 alpha,6 beta-difluoro-11 beta-hydroxy-16 alpha-methyl-3-oxo-androsta-1,4-diene 17 beta-carboxylate;

isopropyl 9 alpha-chloro-6 alpha,6 beta-difluoro-11 beta-hydroxy-16 alpha-methyl-3-oxo-17 alpha-valeryloxyandrosta-1,4-diene 17 beta-carboxylate; and the like.

EXAMPLE 5

This example sets forth a process for preparing alkyl or benzyl 17 alpha-alkanoyloxy-6 alpha,6 beta,9 alpha-trifluoro-11 beta-hydroxy-16 alpha-methyl-3-oxoandrosta-1,4-diene 17 beta-carboxylates.

A. Preparation of methyl 6 alpha,6 beta, 9 alpha-trifluoro-11 beta-hydroxy-16 alpha-methyl-3-oxo-17 alpha-propionyloxyandrosta-1,4-diene 17 beta-carboxylate.

A solution of 10 g of methyl 9 alpha-bromo-6 alpha,-6 beta-difluoro-11 beta-hydroxy-16 alpha-methyl-3-oxo-17 alpha-propionyloxyandrosta-1,4-diene 17 beta-carboxylate prepared in accordance with the process of Example 4, Part A, in 250 ml of DCM containing 10% methanol, is treated dropwise with a 1 M solution of sodium hydroxide in anhydrous methanol, until TLC analysis using 50% ethyl acetate/50% Hexane, shows the reaction to be complete. Then 5 ml of glacial acetic acid is added, and the mixture is concentrated under reduced pressure to a small volume. More methanol is added and the concentration was continued under reduced pressure, until all the DCM is eliminated. Then the mixture is slowly diluted with water up to 2 liters, to form a crystalline precipitate which is collected by filtration and air dried to give methyl 9 beta,11 beta-epoxy-6 alpha,6 beta-difluoro-16 alpha-methyl-3-oxo-17 alpha-propionyloxy-androsta-1,4-diene 17 beta-carboxylate.

A solution of 10 g of the product prepared in this manner in 150 ml of DCM/50 ml of tetrahydrofuran is cooled to −78° using a dry-ice acetone bath and treated with 40 g of anhydrous HF and 5 mls of boron trifluoroide etherate. The mixture is allowed to warm to 0° C. and is maintained at that temperature for 7 hours. The mixture is poured over an excess of aqueous ammonium hydroxide and ice. The resulting mixture is extracted with DCM three times. The combined DCM extracts are combined, washed with water, dried over anhydrous sodium sulfate, filtered, concentrated to dryness, and the residue chromatographed over silica gel in a 75% DCM/25% hexane to yield methyl 6 alpha, 6 beta,9 alpha-trifluoro-11 beta-hydroxy-16 alpha-methyl-3-oxo-17 alpha-propionyloxyandrosta-1,4-diene 17 beta-carboxylate.

B. Similarly, by following in principle the procedure set forth in this example, but substituting other suitable alkyl or benzyl 17 alpha-alkanoyl-9 alpha-bromo-6 alpha,6 beta-difluoro-11 beta-hydroxy-16 alpha-methyl-3-oxoandrosta-1,4-diene 17 beta-carboxylates prepared in accordance with Example 4 for methyl 9 alpha-bromo-6 alpha,6 beta-difluoro-11 beta-hydroxy-16 alpha-methyl-3-oxo-17 alpha-propionyloxyandrosta-1,4-diene 17 beta-carboxylate, other alkyl or benzyl 17 alpha-alkanoyloxy-6 alpha,6 beta,9 alpha-trifluoro-11 beta-hydroxy-16 alpha-methyl-3-oxoandrosta-1,4-diene 17 beta-carboxylates are prepared such as, methyl 17 alpha-acetoxy-6 alpha,6 beta,9 alpha-trifluoro-11 beta-hydroxy-16 alpha-methyl-3-oxoandrosta-1,4-diene 17 beta-carboxylate;

methyl 17 alpha-n-butyryloxy-6 alpha,6 beta,9 alpha-trifluoro-11 beta-hydroxy-16 alpha-methyl-3-oxoandrosta-1,4-diene 17 beta-carboxylate;

methyl 17 alpha-sec-butyryloxy-6 alpha,6 beta,9 alpha-trifluoro-11 beta-hydroxy-16 alpha-methyl-3-oxoandrosta-1,4-diene-17 beta-carboxylate; and methyl 6 alpha,6 beta,9 alpha-trifluoro-17 alpha-n-hexanoyloxy-11 beta-hydroxy-16 alpha-methyl-3-oxoandrosta-1,4-diene 17 beta-carboxylate;

ethyl 6 alpha,6 beta,9 alpha-trifluoro-11 beta-hydroxy-16 alpha-methyl-3-oxo-17 alpha-propionyloxyandrosta-1,4-diene 17 beta-carboxylate;

isopropyl 6 alpha,6 beta,9 alpha-trifluoro-11 beta-hydroxy-16 alpha-methyl-3-oxo-17 alpha-propionyloxyandrosta-1,4-diene 17 beta-carboxylate;

n-propyl 6 alpha,6 beta,9 alpha-trifluoro-11 beta-hydroxy-16 alpha-methyl-3-oxo-17 alpha-propionyloxyandrosta-1,4-diene 17 beta-carboxylate;

t-butyl 6 alpha,6 beta,9 alpha-trifluoro-11 beta-hydroxy-16 alpha-methyl-3-oxo-17 alpha-propionyloxyandrosta-1,4-diene 17 beta-carboxylate;

n-pentyl 6 alpha,6 beta,9 alpha-trifluoro-11 beta-hydroxy-16 alpha-methyl-3-oxo-17 alpha-propionyloxyandrosta-1,4-diene 17 beta-carboxylate;

benzyl 6 alpha,6 beta,9 alpha-trifluoro-11 beta-hydroxy-16 alpha-methyl-3-oxo-17 alpha-propionyloxyandrosta-1,4-diene 17 beta-carboxylate;

4-chlorobenzyl 6 alpha,6 beta,9 alpha-trifluoro-11 beta-hydroxy-16 alpha-methyl-3-oxo-17 alpha-propionyloxyandrosta-1,4-diene 17 beta-carboxylate;

2-fluorobenzyl 6 alpha,6 beta,9 alpha-trifluoro-11 beta-hydroxy-16 alpha-methyl-3-oxo-17 alpha-propionyloxyandrosta-1,4-diene 17 beta-carboxylate;

3-methylbenzyl-6 alpha,6 beta,9 alpha-trifluoro-11 beta-hydroxy-16 alpha-methyl-3-oxo-17 alpha-propionyloxyandrosta-1,4-diene 17 beta-carboxylate;

4-n-propylbenzyl 6 alpha,6 beta,9 alpha-trifluoro-11 beta-hydroxy-16 alpha-methyl-3-oxo-17 alpha-propionyloxyandrosta-1,4-diene 17 beta-carboxylate;

4-ethoxybenzyl 6 alpha,6 beta,9 alpha-trifluoro-11 beta-hydroxy-16 alpha-methyl-3-oxo-17 alpha-propionyloxyandrosta-1,4-diene 17 beta-carboxylate;

4-t-butoxybenzyl 6 alpha,6 beta,9 alpha-trifluoro-11 beta-hydroxy-16 alpha-methyl-3-oxo-17 alpha-propionyloxyandrosta-1,4-diene 17 beta-carboxylate;

2-methoxybenzyl-6 alpha,6 beta,9 alpha-trifluoro-11 beta-hydroxy-16 alpha-methyl-3-oxo-17 alpha-propionyloxyandrosta-1,4-diene 17 beta-carboxylate;

ethyl 17 alpha-acetoxy-6 alpha,6 beta,9 alpha-trifluoro-11 beta-hydroxy-16 alpha-methyl-3-oxoandrosta-1,4-diene 17 beta-carboxylate;

t-butyl 17 alpha-acetoxy-6 alpha,6 beta,9 alpha-trifluoro-11 beta-hydroxy-16 alpha-methyl-3-oxoandrosta-1,4-diene 17 beta-carboxylate;

benzyl 17 alpha-butyryloxy-6 alpha,6 beta,9 alpha-trifluoro-11 beta-hydroxy-16 alpha-methyl-3-oxoandrosta-1,4-diene 17 beta-carboxylate; and the like.

EXAMPLE 6

This example sets forth a process for preparing alkyl or benzyl 17 alpha-alkanoyloxy 9 alpha,11 beta-dichloro-6 alpha, 6 beta-difluoro-17 alpha-hydroxy-16 alpha-methyl-3-oxoandrost-4-ene 17 beta-carboxylates.

A. Preparation of methyl 9 alpha,11 beta-dichloro-6 alpha,6 beta-difluoro-16 alpha-methyl-3-oxo-17 alpha-propionyloxyandrost-4-ene 17 beta-carboxylate.

Thionyl chloride (3.6 grams) is dispersed in 250 ml of carbon tetrachloride at room temperature. Chlorine gas is bubbled through the resulting mixture at room temperature until the molar amount of chlorine dispersed approximates the molar amount of thionyl chloride present. Twenty four (24) g of 21-acetoxy 6 alpha-fluoro-11 beta,17 alpha-dihydroxy-16 alpha-methylpregn-4-ene-3,20-dione is dissolved in 100 ml of methylene chloride containing 4 milliliters of pyridine. The thionyl chloride, chlorine, carbon tetrachloride mixture is then slowly added to the solution at room temperature with stirring. After the addition, the resulting reaction mixture is allowed to stand at room temperature for five minutes. After this time, the reaction mixture is washed with dilute hydrochloric acid and then water to a neutral pH. The washed mixture is then dried over sodium sulfate and the dried mixture evaporated to provide the 21-acetoxy-9 alpha,11 beta-difhloro-6 alpha-fluoro-17 alpha-hydroxy-16 alpha-methylpregn-4-ene-3,20-dione product which is further purified by recrystallization from methylene chloride/hexane.

This compound is then converted into 9 alpha,11 beta-dichloro-6 alpha-fluoro-17 alpha-hydroxy-16 alpha-methyl-3-oxoandrost-4-ene which in turn is converted to methyl 9 alpha,11 beta-dichloro-6 alpha,6 beta-difluoro-16 alpha-methyl-3-oxo-17 alpha-propionyloxyandrosta-1,4-diene 17 beta-carboxylate by procedures set forth in Examples 1 and 2.

B. Similarly, 9 alpha,11 beta-dichloro-6 alpha-fluoro-17 alpha-hydroxy-16 alpha-methyl-3-oxoandrost-4-ene is converted to other alkyl or benzyl 17 alpha-alkanoyloxy 9 alpha,11 beta-dichloro-6 alpha,6 beta-difluoro-16 alpha-methyl-3-oxoandrosta-1,4-diene 17 beta-carboxylates of this invention by following in principle the process of Part A of this example but substituting other alkyl or benzyl iodides for methyl iodide and other alkanoyl anhydrides for propionic anhydride. These include methyl 17 alpha-acetoxy-9 alpha,11 beta-dichloro-6 alpha,6 beta-difluoro-16 alpha-methyl-3-oxoandrosta-1,4-diene 17 beta-carboxylate;

methyl 17 alpha-n-butyryloxy-9 alpha,11 beta-dichloro-6 alpha,6 beta-difluoro-16 alpha-methyl-3-oxoandrosta-1,4-diene 17 beta-carboxylate;

methyl 17 alpha-sec-butyryloxy-9 alpha,11 beta-dichloro-6 alpha,6 beta-difluoro-16 alpha-methyl-3-oxoandrosta-1,4-diene 17 beta-carboxylic acid; and methyl 9 alpha,11 beta-dichloro-6 alpha,6-beta-difluoro-17 alpha-n-hexanoyloxy-16 alpha-methyl-3-oxoandrosta-1,4-diene 17 beta-carboxylate;

ethyl 9 alpha,11 beta-dichloro 6 alpha,6 beta-trifluoro-16 alpha-methyl-3-oxo-7 alpha-propionyloxyandrosta-1,4-diene 17 beta-carboxylate;

isopropyl 17 alpha-acetoxy-9 alpha,11 beta-dichloro-6 alpha,6 beta-difluoro-16 alpha-methyl-3-oxoandrosta 1,4-diene 17 beta-carboxylate;

n-propyl 17 alpha-butyryloxy-9 alpha,11 beta-dichloro-6 alpha,6 beta-difluoro-16 alpha-methyl-3-oxoandrosta-1,4-diene 17 beta-carboxylate;

t-butyl 17 alpha-acetoxy-9 alpha,11 beta-difluoro-6 alpha,6 beta-difluoro-16 alpha-methyl-3 oxoandrosta-1,4-diene 17 beta-carboxylate;

n-pentyl 9 alpha,11 beta-dichloro-6 alpha-6 beta-difluoro-17 alpha-isobutyryloxy-16 alpha-methyl-3-oxoandrosta 1,4-diene 17 beta-carboxylate;

benzyl 9 alpha,11 beta-dichloro 6 alpha,6 beta-difluoro-17 alpha-isopropionyloxy-16 alpha-methyl-3-oxoandrosta 1,4-diene 17 beta-carboxylate;

4-chlorobenzyl 9 alpha,11 beta-dichloro-6 alpha,6 beta-difluoro-16 alpha-methyl-3-oxo-17 alpha-propionyloxyandrosta 1,4-diene 17 beta-carboxylate;

2-fluorobenzyl 9 alpha,11 beta-dichloro-6 alpha,6 beta-difluoro-17 alpha-n-hexanoyloxy-16 alpha-methyl-3-oxoandrosta-1,4-diene 17 beta-carboxylate;

3-methylbenzyl 17 alpha-acetoxy-9 alpha,11 beta-dichloro-6 alpha,6 beta-difluoro-16 alpha-methyl-3-oxoandrosta-1,4-diene 17 beta-carboxylate;

4-n-propylbenzyl 9 alpha,11 beta-dichloro-6 alpha,6 beta-difluoro-16 alpha-methyl-3-oxo-17 alpha-propionyloxyandrosta 1,4-diene 17 beta-carboxylate;

4-ethoxybenzyl 9 alpha-11 beta-dichloro-6 alpha,6 beta-trifluoro-16 alpha-methyl-3-oxo-17 alpha-valeryloxyandrosta 1,4-diene 17 beta-carboxylate;

4-t-butoxybenzyl 9 alpha,11 beta-dichloro-6 alpha,6 beta-difluoro-16 alpha-methyl-3-oxo-17 alpha-propionyloxyandrosta-1,4-diene 17 beta-carboxylate;

ethyl 17 alpha-acetoxy-9 alpha,11 beta-dichloro-6 alpha,6 beta-difluoro-16 alpha-methyl-3-oxoandrosta 1,4-diene 17 beta-carboxylate;

t-butyl 17 alpha-acetoxy-9 alpha,11 beta-dichloro-6 alpha,6 beta-difluoro-16 alpha-methyl-3-oxoandrosta-1,4-diene 17 beta-carboxylate;

benzyl 17 alpha-butyryloxy-9 alpha,11 beta-dichloro-6 alpha,6 beta-difluoro-16 alpha-methyl-3-oxoandrosta-1,4-diene 17 beta-carboxylate; and the like.

EXAMPLE 7

This example sets forth a process for preparing compounds of formula (I) wherein $X^1$ is hydrogen, fluoro, chloro or bromo; $X^2$ is

or also is

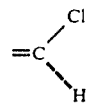

when $X^1$ is chloro; R is hydrogen; $R^1$ is alkanoyl; and $R^2$ is alpha methyl.

A. Preparation of 6 alpha,6 beta,9 alpha-trifluoro-11 beta-hydroxy-16 alpha-methyl-3-oxo-17 alpha-propionyloxyandrosta-1,4-diene 17 beta-carboxylic acid.

A solution of 86 g of 6 alpha,6 beta,9 alpha-trifluoro-11 beta,17 alpha-dihydroxy-16 alpha-methylpregna-1,4-diene-3,20-dione (prepared as taught in U.S. Pat. No. 3,546,215 to Fried) in 1000 ml of methanol plus 86 g of anhydrous potassium carbonate is stirred for about 20 hours while air is bubbled through the solution. The methanol is eliminated under reduced pressure and about 1.5 l of water is added to the residue in the reaction vessel. Additional air is bubbled through this mixture while stirring and additional methanol is added to maintain the volume at about 1.5 l until TLC analysis using 5% methanol/1% acetic acid/94% DCM indicates the reaction is complete. The resulting mixture is acidified with concentrated HCl to pH 2, and the resulting crystalline precipitate is collected by filtration and air dried to yield 6 alpha,6 beta,9 alpha-trifluoro-11 beta,17 alpha-dihydroxy-16 alpha-methyl-3-oxoandrosta-1,4-diene 17 beta-carboxylic acid.

This compound is reacted with propionic anhydride according to the appropriate process of Example 1 to yield 6 alpha,6 beta,9 alpha-trifluoro-11 beta-hydroxy-16 alpha-methyl-3-oxo-17 alpha-propionyloxyandrosta-1,4-diene 17-carboxylic acid.

B. Similarly, by following in principle the procedure of Part A but substituting other appropriate steroids made according to the teachings of U.S. Pat. No. 3,546,215 to Fried for 6 alpha,6 beta-difluoro-11 beta,17 lpha-dihydroxy-16 alpha-methylpregna-1,4-diene-3,20-dione and other alkanoyl anhydrides for propionic anhydride, other 17 alpha-alkanoyl derivatives are obtained.

EXAMPLE 8

This example sets forth a process for preparing compounds of formula (I) wherein $X^1$ is

or also is

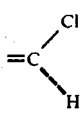

when $X^1$ is chloro; R is alkyl or benzyl; $R^1$ is hydrogen; and $R^2$ is alpha-methyl.

A. Preparation of methyl 6 alpha,6 beta,9 alpha-trifluoro-11 beta,17 alpha-dihydroxy-16 alpha-methyl-3-oxoandrostas-1,4-diene 17 beta-carboxylate.

A suspension of 10 g of 6 alpha,6 beta,9 alpha-trifluoro-11 beta,17 alpha-dihydroxy-16 alpha-methyl-3-oxoandrosta-1,4-diene 17 beta-carboxylic acid prepared according to the process of Example 7, Part A, in 100 ml of dimethylformamide is mixed with 10 g of methyl iodide and stirred in the presence of 10 g of sodium bicarbonate for 12 hours. The reaction mixture is slowly diluted with water to give a precipitate which is collected by filtration and air dried to give methyl 6 alpha,6 beta,9 alpha-trifluoro-11 beta,17 alpha-dihydroxy-16 alpha-methyl-3-oxoandrosta-1,4-diene 17 beta-carboxylate.

B. Similarly, by following in principle the process of Part A of this example but substituting other appropriate steroids of this invention for 6 alpha,6 beta,-9 alpha-trifluoro-1dl beta,17 alpha-dihydroxy-16 alpha-methyl-3-oxoandrosta-1,4-diene 17 beta-carboxylic acid and other alkyl or benzyl iodides for methyl iodide, other alkyl or benzyl carboxylates of this invention are readily prepared.

EXAMPLE 9

This example sets forth a process for preparing the phenyl 17 beta-carboxylate of this invention according to the principles set forth in Neilakantan, et al, *New Reagents for the Preparation of Depsides*, Tetrahedron 21, 3531-3536 (1965).

A mixture of approximately equimolar amounts (0.002) of 6 alpha,6 beta,9 alpha-trifluoro-11 beta-hydroxy-16 alpha-3-oxo-17 alpha-propionyloxyandrosta-1,4-diene 17 beta-carboxylic acid and phenol in 50 ml of dry ether is prepared. An approximately equimolar quantity of dicyclohexylcarbodiimide is added, the solution is stirred for 6 hours at room temperature and left overnight. The solvent is evaporated and the residue is taken up in dichloromethane, washed with water, filtered, dried and the solvent evaporated to give phenyl 4,6 alpha,9 alpha-trifluoro-11 beta-hydroxy-16 alpha-methyl-3-oxo-17 alpha-propionyloxyandrosta-1,4-diene 17 beta-carboxylate.

EXAMPLE 10

By following in principle the procedures set forth in Examples 1-9 but substituting the corresponding 16 beta-methyl steroid starting material for the 16 alpha-methyl steroid starting material, the corresponding 16 beta-methyl steroids of this invention are obtained such as 6 alpha,6 beta,9 alpha-trifluoro-11 beta,17 alpha-dihydroxy-16 beta-methyl-3-oxo-androst-4-ene 17 beta-carboxylic acid and the corresponding 17 alpha-alkanoyloxy derivatives along with the alkyl, benzyl or phenyl-17 beta-carboxylates.

EXAMPLE 11

By following in principle the procedures set forth in Examples 1-4 but substituting the corresponding 16-unsubstituted steroid starting material for the 16 alpha-methyl steroid starting material, the corresponding 16-unsubstituted steroids of this invention are obtained, such as 6 alpha,6 beta,9 alpha-trifluoro-11 beta,17 alpha-dihydroxy-3-oxo-androst-4-diene 17 beta-carboxylic acid and the corresponding alkyl, benzyl or phenyl 17 beta-carboxylates as well as the 17-alpha-alkanoyloxy derivatives.

EXAMPLE 12

This example sets forth a process for preparing an 11-keto compound of this invention by oxidizing any of the 11 beta-hydroxy steroids set forth in Examples 1-7.

One g of methyl 6 alpha,6 beta,9 alpha-trifluoro-11 beta-hydroxy-16 alpha-methyl-3-oxo-17 alpha-propionyloxyandrosta-1,4-diene-17 beta-carboxylate is dissolved in 50 ml of acetone and treated at room temperature with Jone's reagent (chromic anhydride in dilute sulfuric acid) dropwise until TLC indicates the absence of starting material. The mixture is treated with five drops of isopropyl alcohol to destroy any excess of reagent, then diluted with 50 ml of water and the mixture concentrated under vacuum under reduced pressure to give a crystalline material, namely methyl 6 alpha,6 beta,9 alpha-trifluoro-16 alpha-methyl-3-oxo-17 alpha-propionyloxyandrosta-1,4-diene-17 beta-carboxylate.

EXAMPLE 13

This example sets forth a process for converting androsta-1,4-diene 17 beta-carboxylic acids and their derivatives of this invention to the corresponding androst-4-ene carboxylic acids and the respective derivatives.

A solution of 25 mg of tris-(triphenylphosphine) chloro-rhodium in 6 ml of benzene and 15 ml of ethanol is stirred under hydrogen for 60 minutes. Methyl 6 alpha,6 beta,9 alpha-trifluoro-11 beta-hydroxy-6 alpha-methyl-3-oxo-17 alpha-propionyloxyandrosta-1,4-diene-17 beta-carboxylate (244 mg) is added and the resulting solution is stirred under hydrogen at room temperature at atmospheric pressure. After hydrogen uptake is complete, the solution is evaporated to dryness and the residue taken up in a mixture of petroleum ether and methylene chloride. The pure product is isolated by column chromatography on silica gel to give methyl 4,6 alpha,9 alpha-trifluoro-11 beta-hydroxy-16 alpha-methyl-3-oxo-17 alpha-propionyloxyandrost-4-ene 17 beta-carboxylate.

Similarly, by substituting other androsta-1,4-diene steroids of this invention made according to Examples 3-12 for methyl 6 alpha,6 beta,9 alpha-trifluoro-11 beta-hydroxy-16 alpha-methyl-3-oxo-17 alpha-propionylandrosta-1,4-diene 17 beta-carboxylate other corresponding androst-4-ene steroids are prepared.

What is claimed is:

1. A compound chosen from those represented by the formula

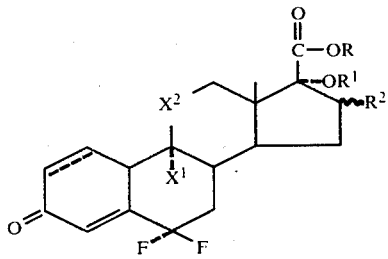

(I)

wherein
X¹ is chloro;
X² is

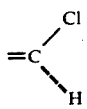

R is hydrogen, alkyl or 1 through 6 carbon atoms optionally substituted with one of halo, phenyl or benzyl ring chosen from the group consisting of alkyl of 1 through 4 carbon atoms, alkoxy of 1 through 4 carbon atoms and halo;

R¹ is hydrogen or alkanoyl of 2 through 6 carbon atoms;

R² is hydrogen, alpha-methyl or beta-methyl; and the broken line between C-1 and C-2 represents a double or a single bond.

2. The compound of claim 1 wherein R² is alpha-methyl.

3. The compound of claim 2 wherein R is hydrogen, alkyl of 1 to 6 carbon atoms, phenyl or benzyl and R¹ is hydrogen or alkanoyl of 1 through 6 carbon atoms.

4. The compound of claim 3 wherein X¹ is chloro and X² is

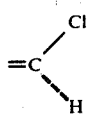

5. The compound of claim 4 wherein the bond between C-1 and C-2 is a double bond, R is methyl and R¹ is propionyl, namely methyl 9 alpha, 11 beta-dichloro-6 alpha, 6 beta-difluoro-16 alpha-methyl-3-oxo-propionyloxyandrosta-1,4-diene 17 betacarboxylate.

6. An anti-inflammatory pharmaceutical composition which comprises an effective amount of a compound of claim 1 in combination with a suitable pharmaceutical excipient.

7. A process for treating an inflamed condition in a mammal which comprises adminstering an effective amount of a compound of claim 1 to said mammal.

8. A process for treating an inflamed condition in a mammal which comprises administering an effective amount of a compound of claim 1 to said mammal.

* * * * *